(12) United States Patent
Madison

(10) Patent No.: US 6,354,293 B1
(45) Date of Patent: Mar. 12, 2002

(54) BREATHING HUMIDIFIER

(76) Inventor: Foster E. Madison, 1329 Camaron St., Lancaster, CA (US) 93535

(*) Notice: Subject to any disclaimer, the term of this patent is extended or adjusted under 35 U.S.C. 154(b) by 0 days.

(21) Appl. No.: 09/524,331

(22) Filed: Mar. 13, 2000

Related U.S. Application Data

(60) Provisional application No. 60/124,516, filed on Mar. 16, 1999.

(51) Int. Cl.$^7$ ............................................. A61M 15/00
(52) U.S. Cl. ............................. 128/204.13; 128/206.11; 128/207.18
(58) Field of Search .................. 128/203.19, 203.22, 128/206.11, 207.18, 204.12, 204.13

(56) References Cited

U.S. PATENT DOCUMENTS

| | | | | |
|---|---|---|---|---|
| 238,793 A | * | 3/1881 | Leslie | 128/203.22 |
| 369,019 A | * | 8/1887 | McMaster | 128/204.12 |
| 470,011 A | * | 3/1892 | Roberts | 128/203.22 |
| 639,808 A | * | 12/1899 | Gardener et al. | |
| 780,709 A | | 1/1905 | Craig | 128/200.11 |
| 834,184 A | * | 10/1906 | Caldwell | 128/203.22 |
| 844,097 A | * | 2/1907 | Caldwell | 128/203.22 |
| 888,869 A | * | 5/1908 | Clark | 128/203.22 |
| 1,056,255 A | * | 3/1913 | Cadman | |
| 1,112,312 A | * | 9/1914 | Oliva | 128/203.19 |
| 1,155,608 A | * | 10/1915 | Nieschang | |
| 1,278,342 A | * | 9/1918 | Heimberg | 128/203.22 |
| 1,340,662 A | * | 5/1920 | Lobl | 128/203.22 |
| 1,442,253 A | * | 1/1923 | Cooper | 128/203.22 |
| 1,483,572 A | * | 2/1924 | Clark | |
| 1,740,083 A | * | 12/1929 | Galvin | 128/204.12 |
| 1,948,945 A | | 2/1934 | Seijo | 128/146 |
| 2,208,633 A | * | 7/1940 | Heidbrink | |
| 2,215,188 A | * | 9/1940 | Parks | |
| 2,277,390 A | * | 3/1942 | Crespo | 128/204.12 |
| 2,439,855 A | * | 4/1948 | Mortensen | 128/206.11 |
| 2,763,263 A | * | 9/1956 | Ellman | |
| 3,393,677 A | * | 7/1968 | Echard | 128/203.25 |
| 3,513,844 A | * | 5/1970 | Smith | |
| 3,612,049 A | * | 10/1971 | Monson | 128/203.19 |
| 3,724,459 A | * | 4/1973 | Congro | 128/203.22 |
| 3,902,486 A | * | 9/1975 | Guichard | 128/204.13 |
| 3,929,128 A | | 12/1975 | Pekkariuen | 128/194 |
| 3,965,894 A | | 6/1976 | Fisher | 128/194 |
| 4,150,071 A | | 4/1979 | Pecina | 261/78 |
| 4,267,831 A | * | 5/1981 | Aguilar | 128/203.14 |
| 4,491,130 A | | 1/1985 | Pasternack | 128/202.26 |
| 4,566,450 A | | 1/1986 | Brossman, Jr. | 128/200.11 |
| 4,683,869 A | | 8/1987 | Wilcox | 126/204 |
| 4,753,233 A | * | 6/1988 | Grimes | 128/203.22 |
| 4,941,467 A | | 7/1990 | Takata | 128/203.12 |
| 4,995,384 A | * | 2/1991 | Keeling | 128/207.18 |
| 5,438,978 A | | 8/1995 | Hardester | 128/201.13 |
| 5,526,806 A | * | 6/1996 | Sansoni | 128/206.11 |

FOREIGN PATENT DOCUMENTS

| | | | |
|---|---|---|---|
| DE | 415966 | * | 7/1925 |
| GB | 27450 | * | 8/1904 |
| GB | 221121 | * | 4/1924 |

* cited by examiner

*Primary Examiner*—Aaron J. Lewis
(74) *Attorney, Agent, or Firm*—Dennis W. Beech

(57) ABSTRACT

The breathing humidifier is a reservoir containing a sponge and water. The reservoir is generally shaped to fit the contour of the users face between the upper lip and the nose. The sponge is shaped to fit against the nostril openings. Two openings are located at the bottom of the reservoir into which a gas supply cannula may be inserted. When gas such as oxygen is supplied to the breathing humidifier the gas passes through the water-sponge and heat environment to exit into the nose.

4 Claims, 2 Drawing Sheets

BREATHING HUMIDIFIER

CROSS-REFERENCE TO RELATED APPLICATIONS

This application claims the benefit of U.S. Provisional application Ser. No. 60/124,516 filed Mar. 16, 1999.

BACKGROUND OF THE INVENTION

1. Field of the Invention

The present invention relates to devices used to humidify oxygen, air or other gases that are supplied in to persons such as a patient requiring assistance in breathing.

2. Description of Related Art

Generally devices used for assisted breathing have nasal cannula with prongs or outlet ports which fit in the users nostrils. If gas such as oxygen flows directly from the gas source to the user, the gas may be excessively dry and thereby cause further respiratory problems. Current practice is to pass the gas through a bottle containing water or other fluid to increase the moisture content prior to application to the user. Such an apparatus is disclosed in U.S. Pat. No. 3,929,128, Issued Dec. 30, 1975.

These types of devices are cumbersome and may not be appropriate for individuals outside of use in a health care facility. Many persons who must have oxygen added to their breathing of air simply use an oxygen tank with a tube for direct flow to the nose or mouth.

The instant invention provides a humidifying element which is retained under the users nose. The oxygen or other gas is passed through the breathing humidifier into the users nostrils. The compact humidifying element is simple and easily transportable. In addition the warmth from the users breathing and body heats the humidified gas such that cool, dry gas is not introduced into the lungs.

SUMMARY OF THE INVENTION

One object of the invention is to humidify gas being supplied to a human user. Another object is a humidifying element which is easy to transport by a user. A further object is to warm the gas prior to inhalation by the user. An additional object is to allow use with existing gas source supply cannula.

In accordance with the description presented herein, other objectives of this invention will become apparent when the description and drawings are reviewed.

DESCRIPTION OF THE PREFERRED EMBODIMENT

The breathing humidifier has a reservoir shaped to rest easily under the users nose. There is a shaped sponge placed in the reservoir. Two apertures are provided into which the nasal tubes of a breathing cannula may be inserted. In use the reservoir has water introduced therein.

Figure 1:
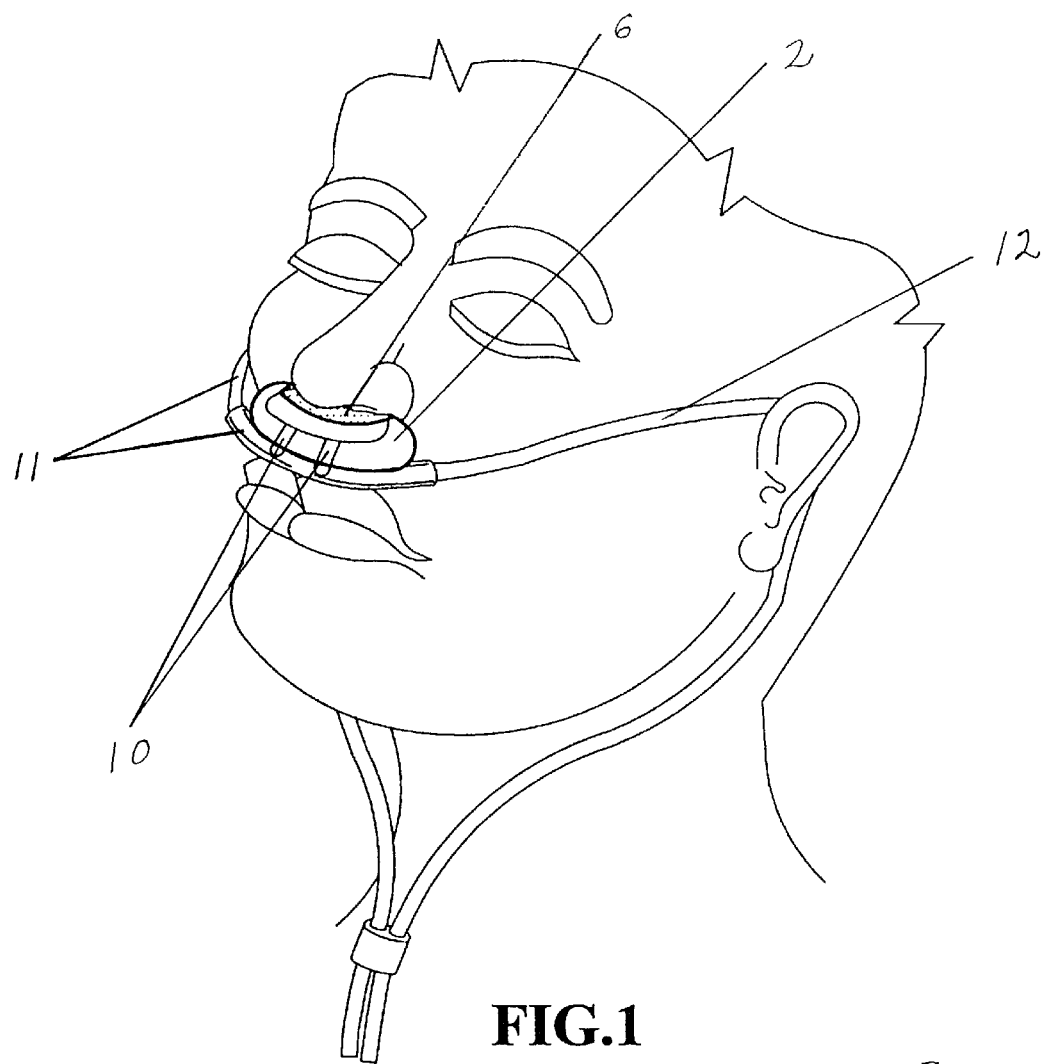
FIG. 1 illustrates a perspective view of the breathing humidifier attached to a nasal cannula and positioned under the nose of a user.
Figure 2:
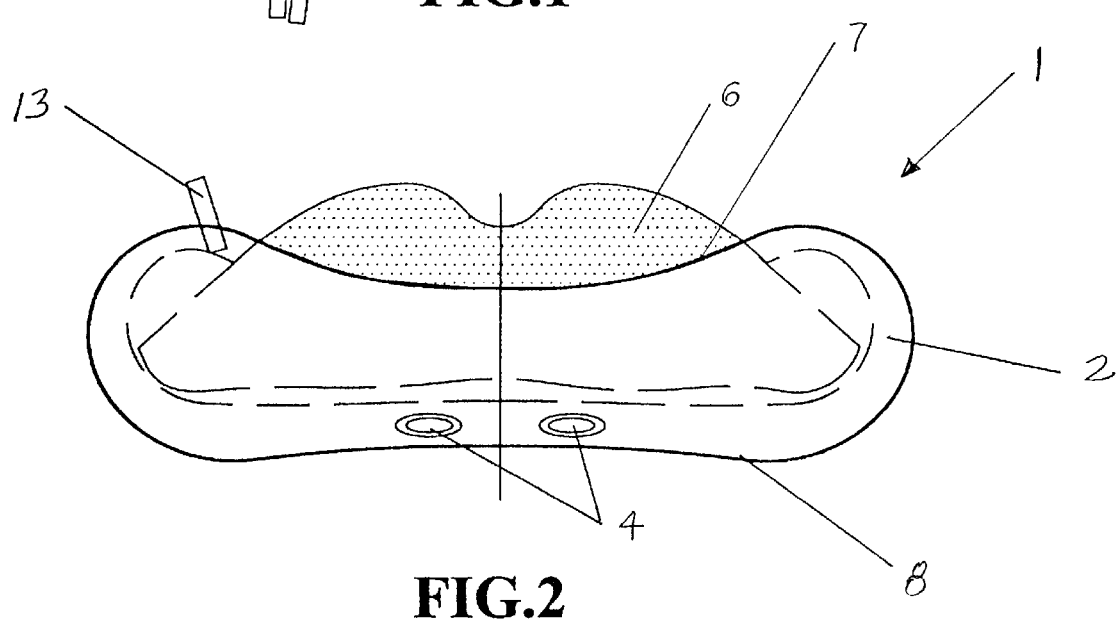
FIG. 2 illustrates a front elevation view of the device.
Figure 3:
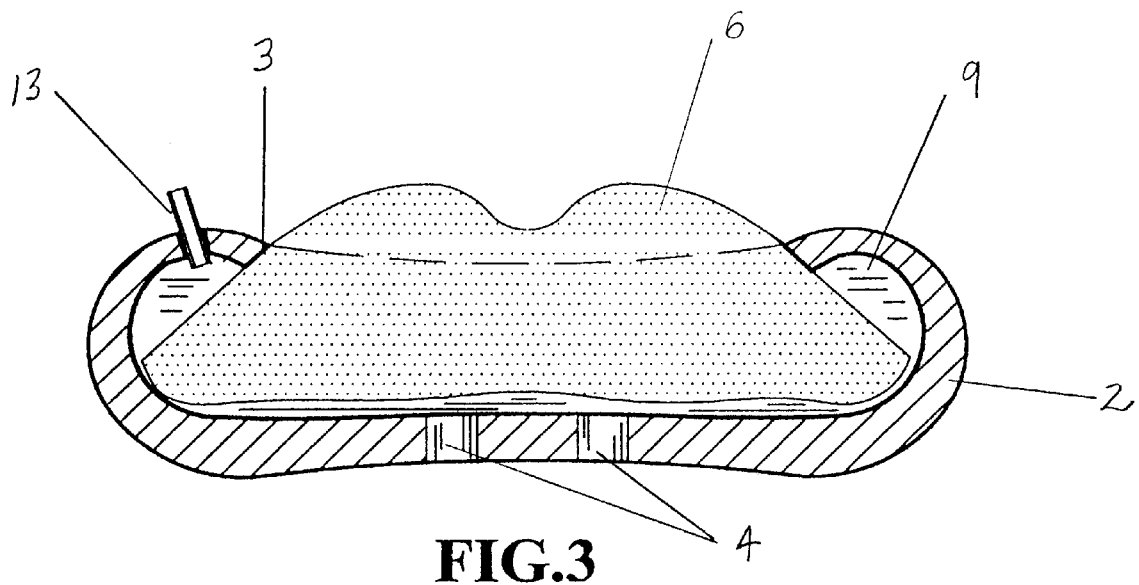
FIG. 3 illustrates a cross sectional view of the breathing humidifier.
Figure 4:
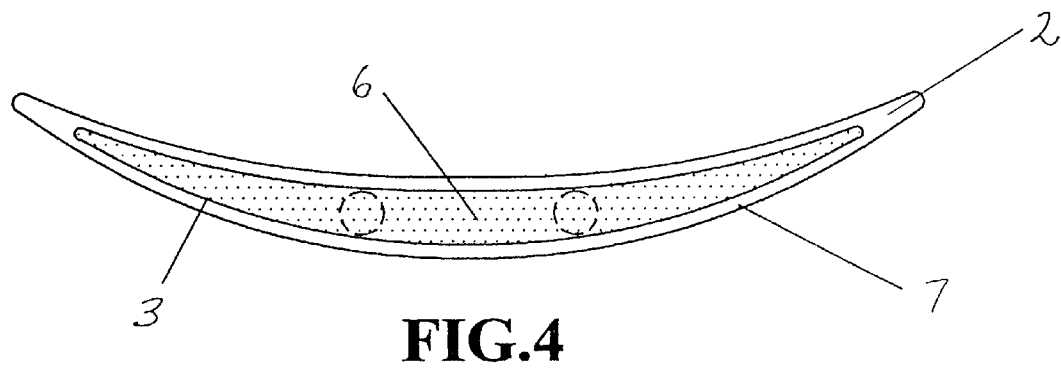
FIG. 4 illustrates a top plan view of the invention.
Figure 5:
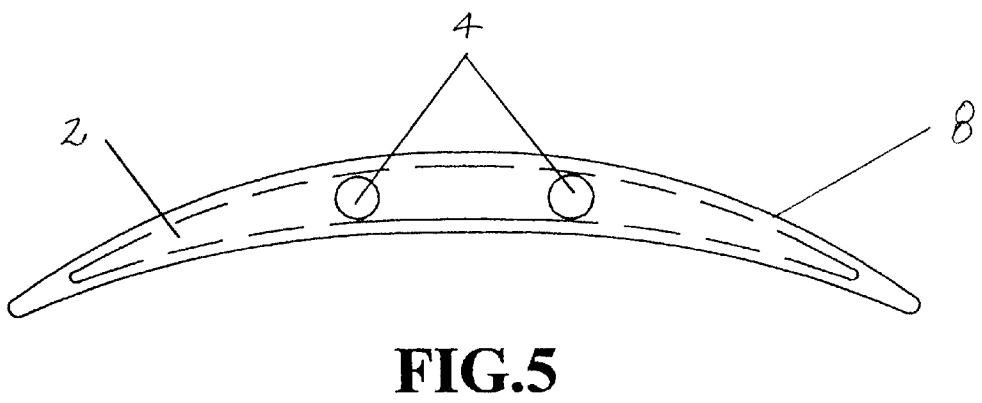
FIG. 5 illustrates a bottom view of the device.

Referring to FIGS. 1 through 5, the breathing humidifier (1) has a reservoir (2) with sponge aperture (3) and tube apertures (4). The breathing humidifier (1) as viewed in the front elevation view is shaped to fit above the users upper lip and under the nose, see FIGS. 1 and 2. The device has a generally crescent shape as viewed from the top (7) or bottom (8).

While this shape is preferred to allow a close fit to the users face, other shapes would also be useable, such as, rectangular non-crescent shape as well as others which are compact to fit between the lip and nose. Such shapes would not normally fit the contour of the face. If additional reservoir capacity is required a larger element may be used which may require use of straps around the users head to retain the breathing humidifier. For larger reservoirs a mask around the reservoir with straps for retention is also feasible.

A sponge (6) is inserted into the reservoir (2) such that a portion of the sponge (6) extends upwardly through the reservoir aperture (3). The exposed portion of the sponge (6) is shaped to easily fit under the nostrils of the users nose. The shape of the reservoir (2) allows the breathing humidifier (1) to be positioned under the nose, against the face and above the upper lip of the user. In use, the reservoir (2) is filled to the desired level with water (9). The nasal tubes (10) of a nasal cannula (11) are inserted into the tube apertures (4). The nasal cannula (11) supply tubes (12) are then located around the users head and over the ears as is understood in the art. This positioning serves to retain the breathing humidifier (1) under the users nose. The supply tubes (12) are then connected to a gas source (not shown) such as an oxygen bottle.

The sponge (6) absorbs water to create a moist environment. The supplied gas passes through the water-sponge environment thereby introducing moisture into the gas. Additionally the reservoir (2) and contents are kept warm by means of the users breathing and body temperature. This combination provides the user with warmed, humidified gas for breathing as compared to cold, dry gas if supplied directly.

A water tube (13) may be provided for attachment to an external water supply (not shown). The water supply system would be designed to maintain the water level in the reservoir by for example capillary action.

While the invention has been particularly shown and described with respect to the illustrated and preferred embodiments thereof, it will be understood by those skilled in the art that the foregoing and other changes in form and details may be made therein without departing from the spirit and scope of the invention.

I claim:

1. A device for humidifying gas to be inhaled by a user comprising:

a reservoir having a sponge aperture formed in a top thereof and a tube aperture formed in a bottom thereof;

a fluid contained in the reservoir;

a sponge inserted into the reservoir and immersed in the fluid with a portion thereof extending out of the reservoir through the sponge aperture for placement under a user's nostrils;

the sponge positioned in the reservoir such that a gas from a gas source introduced through the tube aperture passes through the immersed sponge thereby introducing moisture into the gas prior to exiting the reservoir; and a means to retain the reservoir under a user's nose.

2. The device as in claim 1 wherein the means to retain is a cannula nasal tube inserted in the tube aperture and a cannula supply tube placed over the users ear.

3. The device as in claim 1 wherein the reservoir is crescent shaped for fitting between the user upper lip and nose nostril openings and is contoured to fit the user face.

4. The device as in claim 1 wherein there is a water tube formed in the reservoir to which a water supply is attachable.

* * * * *